United States Patent [19]
Hashii et al.

[11] Patent Number: 5,359,203
[45] Date of Patent: Oct. 25, 1994

[54] LASER OLB APPARATUS AND METHOD OF MOUNTING SEMICONDUCTOR DEVICE

[75] Inventors: Mitsuya Hashii; Haruo Shimamoto; Hideya Yagoura, all of Itami, Japan

[73] Assignee: Mitsubishi Denki Kabushiki Kaisha, Tokyo, Japan

[21] Appl. No.: 70,242

[22] Filed: Jun. 2, 1993

[30] Foreign Application Priority Data

Jun. 3, 1992 [JP] Japan .................. 4-142809

[51] Int. Cl.5 .................................... G01N 21/86
[52] U.S. Cl. ................... 250/561; 219/121.83; 219/121.64
[58] Field of Search ................. 250/561, 562; 219/121.64, 121.63, 121.83; 356/237, 394, 376

[56] References Cited
U.S. PATENT DOCUMENTS 5,008,512 4/1991 Spletter et al. .................. 219/121.64
5,168,141 12/1992 Tosjian et al. .................. 219/121.83

Primary Examiner—David C. Nelms
Assistant Examiner—K. Shami
Attorney, Agent, or Firm—Leydig, Voit & Mayer

[57] ABSTRACT

A laser OLB apparatus includes an XY table; a bonding laser source for irradiating bonding parts between bonding lands of a substrate and leads of a semiconductor device located on the substrate thereby bonding the bonding parts; a recognition device for recognizing whether the leads of the semiconductor device are free of flexure and deviation; and a control unit for controlling the XY table and the laser source so that bonding is conducted only when the recognition device has recognized that the leads are free of flexure and deviation.

23 Claims, 14 Drawing Sheets

LASER OLB APPARATUS AND METHOD OF MOUNTING SEMICONDUCTOR DEVICE

BACKGROUND OF THE INVENTION

1. Field of the Invention

This invention relates to a laser OLB (Outer Lead Bonding) apparatus for mounting a semiconductor device by use of laser beams and such a mounting method.

2. Description of the Related Art

FIGS. 20 and 21 each illustrate a mounting stage unit of a conventional laser OLB apparatus. The laser OLB apparatus recognizes recognition marks 4 of a substrate 3 and thus locates the substrate 3 on a stage 6. After a bonding agent 7 has been applied to this substrate 3, the laser OLB apparatus recognizes outer leads 2 and locates an IC package 1 on the substrate 3. The IC package 1 is then temporarily fixed to the substrate 3 with the bonding agent 7. Subsequently, a plurality of outer leads 2 are irradiated with laser beams 8 and bonded one by one to bonding lands. Note that irradiating positions of the laser beams are programmed beforehand in the laser OLB apparatus.

In the conventional laser OLB apparatus, however, when the IC package 1 is mounted on the substrate 3, there exist some outer leads that are buckled as in the case of an outer lead 2a shown in FIG. 20 and thereby deviate in position from the corresponding bonding lands of the substrate 3. Even in such a state, the irradiation of the laser beams is effected based on preprogrammed patterns. For this reason, there arises a problem that the operation proceeds to the next step even if ill-bonded outer leads 2 are produced. Further, there is also a possibility of forming the ill-bonded outer leads. This is derived from the following reason. Even when there is no flexure in the outer leads 2, the pitches of the outer leads 2 and of the bonding lands of the substrate 3 have some variation in terms of manufacturing processes, and yet the preprogrammed laser beam irradiation is conducted while ignoring these variations.

Further, in some cases, the outer leads 2 are bonded in a state where the IC package 1 is pressed against the substrate 3 by use of an arm and thus fixed thereto instead of temporarily fixing the IC package 1 with the bonding agent 7. In a QFP (Quad Flat Package), however, where the outer leads extend from the four sides of the package body, the following problem is induced. If the irradiation of the laser beams is performed with the IC package being pressed against on the substrate 3 by an arm 5, some leads are overshadowed by the arm 5 and thereby receive no laser beam energy. It is difficult to bond all the outer leads 2.

SUMMARY OF THE INVENTION

It is a primary object of the present invention, which has been devised to obviate the problems described above, to provide a laser OLB apparatus and a mounting method that recognize defective leads and mount ICs with a high reliability.

According to one aspect of the invention, there is provided a laser OLB apparatus comprising: an XY table; a bonding laser source for irradiating, with laser beams, bonding parts between bonding lands of a substrate and leads of a semiconductor device located on said substrate, thus bonding the bonding parts; a light source for illuminating the bonding part between the leads and the bonding lands with light for determining bonding conditions; a device for determining the bonding conditions of the bonding parts on the basis of the reflected light from the bonding parts between the leads and the bonding lands; and a control unit for controlling the XY table and the bonding laser source on the basis of a determination made by the device.

According to another aspect of the invention, there is provided a method of mounting a semiconductor device comprising the steps of: irradiating bonding parts between leads of the semiconductor device and bonding lands with bonding laser beams and thus bonding the bonding parts; illuminating the bonding parts between the leads and the bonding lands with light for determining bonding conditions; and determining the bonding conditions of the bonding parts on the basis of the light reflected from the bonding parts between the leads and the bonding lands.

BRIEF DESCRIPTION OF THE DRAWINGS

Other objects and advantages of the present invention will become apparent during the following discussion in conjunction with the accompanying drawings, in which.

DESCRIPTION OF THE PREFERRED EMBODIMENTS

Embodiments of this invention will hereafter be discussed with reference to the accompanying drawings.

Figure 1:
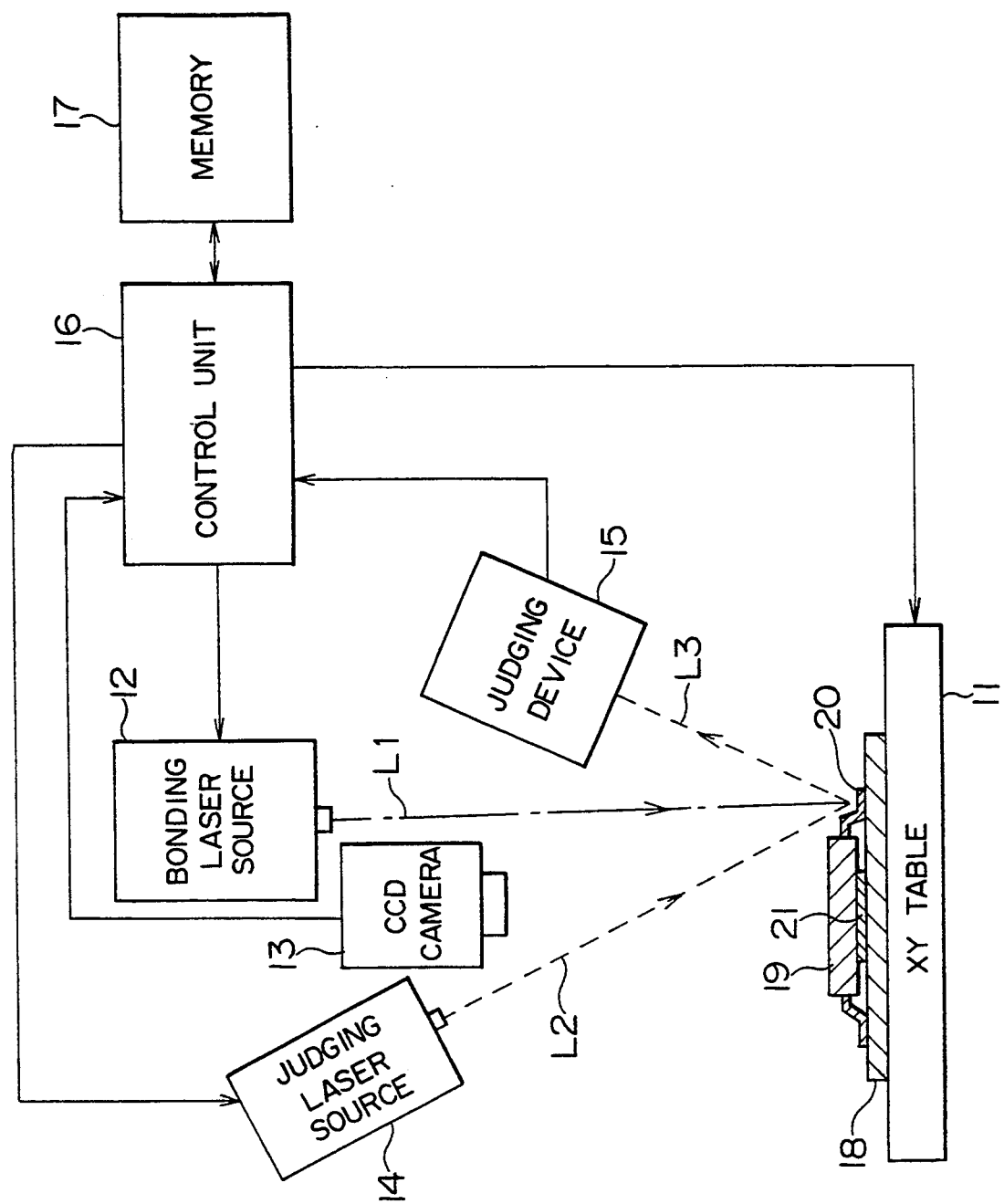
FIG. 1 is a view illustrating a laser OLB apparatus according to one embodiment of this invention.

Paying attention first to FIG. 1, a bonding laser source 12 and a CCD camera 13 serving as a recognition device are disposed above an XY table 11. Provided opposite the XY table 11 are a laser source 14 as a light source for emitting illumination light for determining a bonding state and a judging device 15 for determining the bonding state from the light reflected from a bonding part. Connected to a control unit are the XY table 11, a bonding laser source 12, a CCD camera 13, the laser source 14 and the judging device 15. Further, a memory 17 is also connected to the control unit 16. This memory 17 stores a program of irradiation patterns of the laser beams emitted from the bonding laser source 12 on the basis of a configuration of a semiconductor device and pitches of outer leads.

Next, the operation thereof will be explained. To start with, recognition marks (not shown) on a substrate 18 are recognized through the CCD camera 13. The substrate 18 is placed on the XY table 121 and located. After a bonding agent 21 has been applied to the substrate 18, outer leads 20 of an IC package 19 are recognized through the CCD camera 19. The IC package 19 is thereby located on the substrate 18 and temporarily fixed with the bonding agent 21. When recognizing the outer leads 20 of the IC package 19, the control unit 16 detects defective leads that are bent or deviated. The memory 17 stores data concerning these leads.

Thereafter, the control unit 16 controls the XY table 11 and the bonding laser source 12 on the basis of an irradiation pattern program stored in the memory 17. The bonding laser source 12 thus sequentially irradiates bonding parts between the outer leads 20 of the IC package 19 and bonding lands (unillustrated) of the substrate 18 with bonding laser beams L1. The outer leads 20 are bonded one by one to the bonding lands of the substrate 18. At this time, the outer leads 20 recognized to be defective through the CCD camera 13 are not irradiated with the bonding leaser beams L1. Only the normal outer leads 20 are bonded to the bonding lands corresponding thereto.

When bonding all the normal outer leads 20, the defective leads are corrected and set in normal positions corresponding to the bonding lands. Only the corrected outer leads 20 are irradiated this time with the bonding leaser beams L1. These outer leads 20 are bonded to the bonding lands of the substrate 18.

Next, the Judging laser source 14 irradiates the surface of the outer lead 20 of the bonding part with a Judging laser beam L2. Light ray L3 reflected from the bonding part and direct radiation are caught by the Judging device 15. An output of the Judging laser beam L2 is set within a range so as not to influence the bonding part. The judging device 15 measures the intensity of the light received from the bonding part. Based on a result thereof, the judging device 15 judges whether the bonding part is in an ill- or well-bonded state.

Figure 2A:
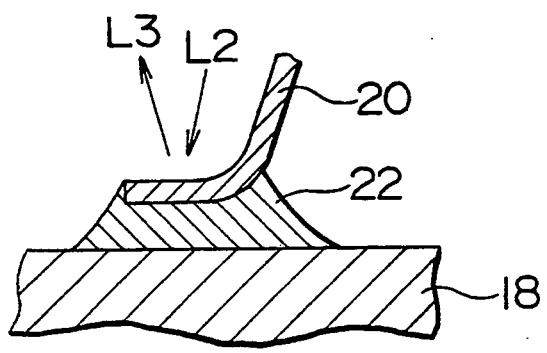
FIG. 2A is a sectional view showing a well-bonded state.
Figure 2B:
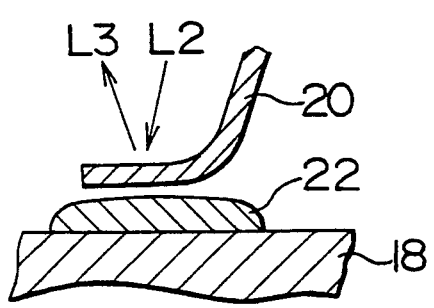
FIG. 2B is a sectional view showing an ill-bonded state.

Herein, the principle of Judging the bonding conditions will be explained. As illustrated in FIG. 2A, if solder is adhered as a bonding land 22 onto the substrate 18 and the outer lead 20 of the IC package 19 are bonded well, there is a good thermal conduction from the outer lead 20 to the substrate 18. Consequently, the heat evolved in the outer lead 20 due to irradiation by the bonding laser beam L1 immediately escapes to the substrate 18. In contrast with this, as shown in FIG. 2B, if the outer lead 20 is ill bonded to the bonding land 22, the thermal conduction from the outer lead 20 to the substrate declines. The temperature of the surface of the outer lead 20 becomes higher than in FIG. 2.

Figure 3:
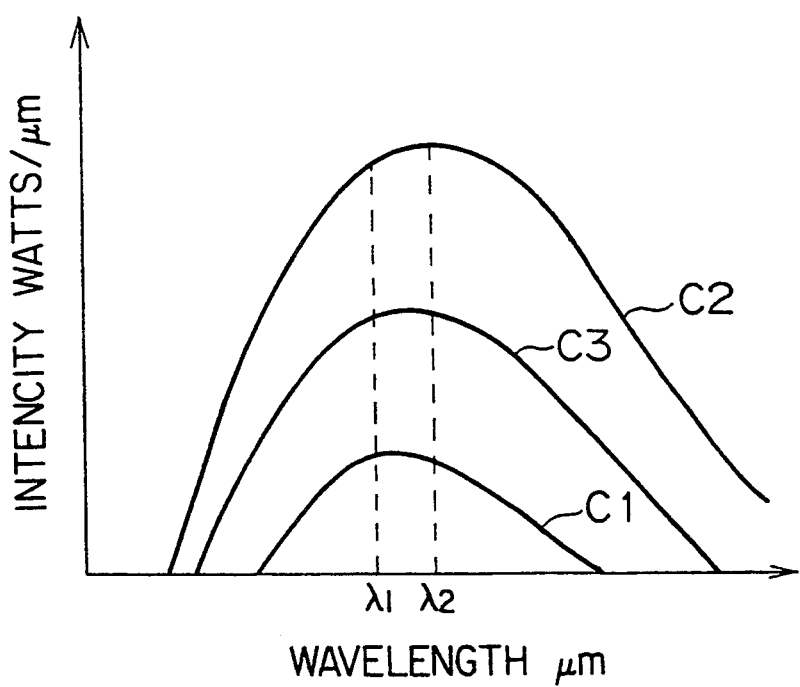
FIG. 3 is a chart showing the principle for determining bonding conditions.

For this reason, the Judging device 15 receives the light reflected L3 from the bonding part and the direct radiation as well. The Judging device 15 takes a distribution of intensities thereof. A curve C1 in FIG. 3 represents a distribution in the well-bonded state, whereas a curve C2 in FIG. 3 indicates a distribution of large intensities in the ill-bonded state. Then, the intensities of light from a wavelength $\lambda_1$ to a wavelength $\lambda_2$ are measured. A threshold value as shown by a curve C3 is prepared. The bonding conditions can be thereby judged.

Note that the bonding conditions can be similarly Judged even by irradiating not the surface of the outer lead 20 but the bonding land 22 of the substrate 18 obliquely with the judging laser beam L2. In this case, however, the temperature is higher in the well-bonded bonding part than in the ill-bonded one.

Further, light for judging the bonding conditions is not restricted to a laser beam, but light sources other than a laser source may be available. Moreover, the bonding laser source 12 is employed commonly as a light source for judging the bonding conditions. It is also possible to effect, when judged, the irradiation of the judging laser having an output decreased to below that of the bonding laser beam L1. Besides, the bonding conditions can be judged even by using only the detected radiation because of irradiation with the bonding laser beam L1.

As a result of judging the bonding conditions in the manner discussed above, the bonding part judged as an ill-bonded part is again bonded by the irradiation of the bonding laser beam L1 from the bonding laser source 12.

Figure 4:
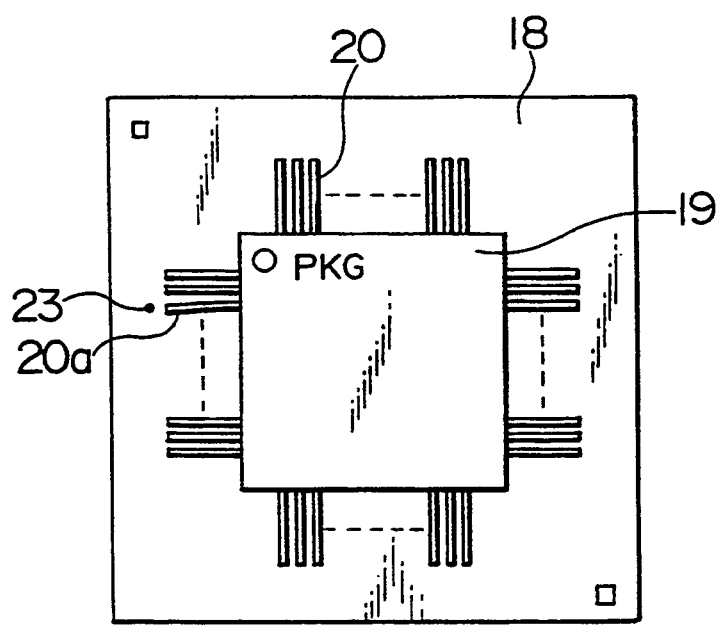
FIG. 4 is a diagram illustrating marking on a substrate.

Note that, as illustrated in FIG. 4, a visual point indication mark 23 may be formed. This formation involves irradiating a substrate part with the laser beam L1 emitted from the bonding laser source 12, this substrate part corresponding to the outer lead 20a recognized as defective through the CCD camera 13. With this arrangement, the lead bonded after being corrected can be checked out in a concentrated manner in the step of visual checkout. The reliability on mounting can be therefore improved. Similarly, marking may be provided in the vicinity of the lead judged as an ill-bonded one by means of the judging device 15. A marking method may include marking with an ink so that the mark is removed by washing in addition to laser marking.

Figure 5:
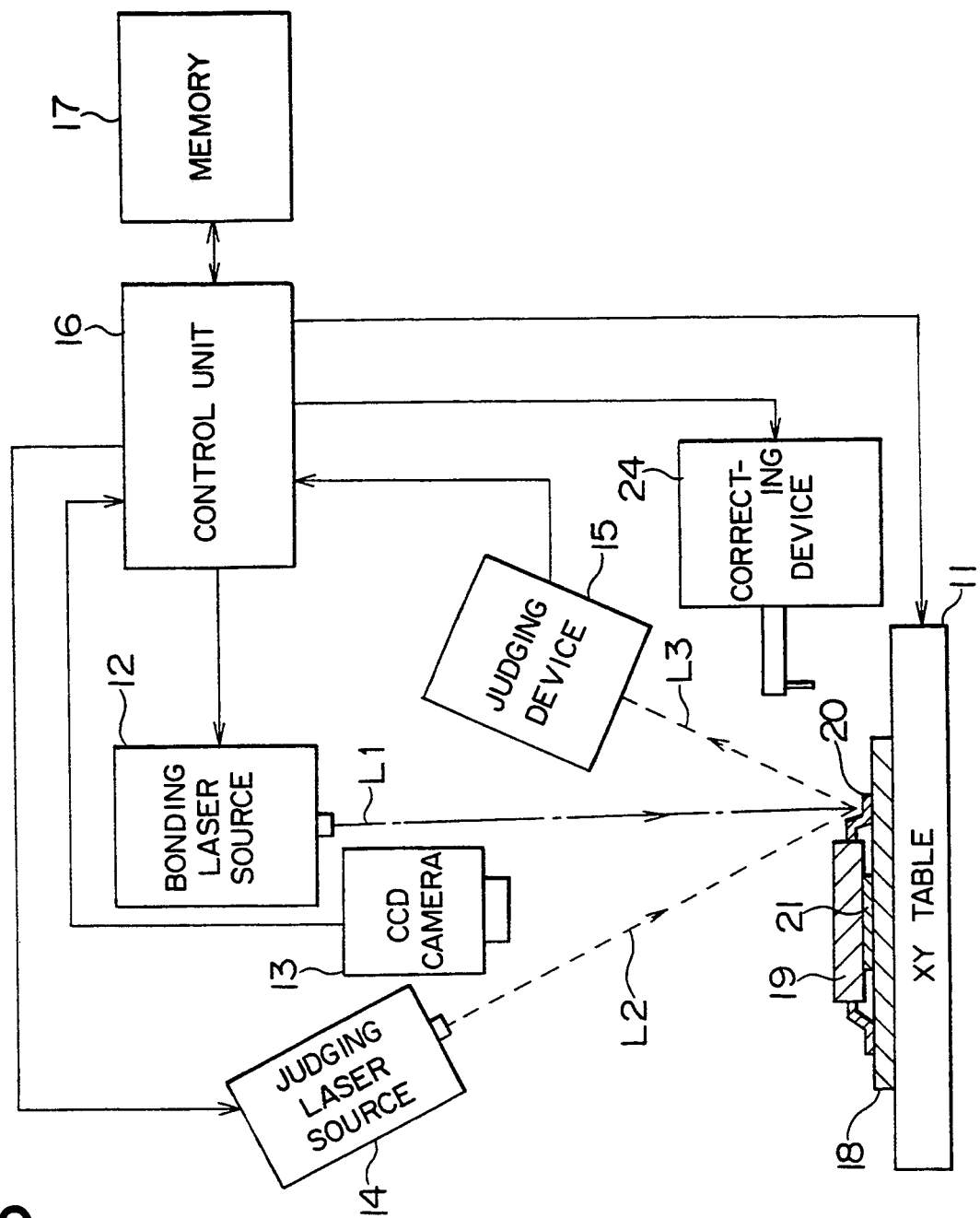
FIG. 5 is a view illustrating a laser OLB apparatus according to another embodiment.
Figure 6:
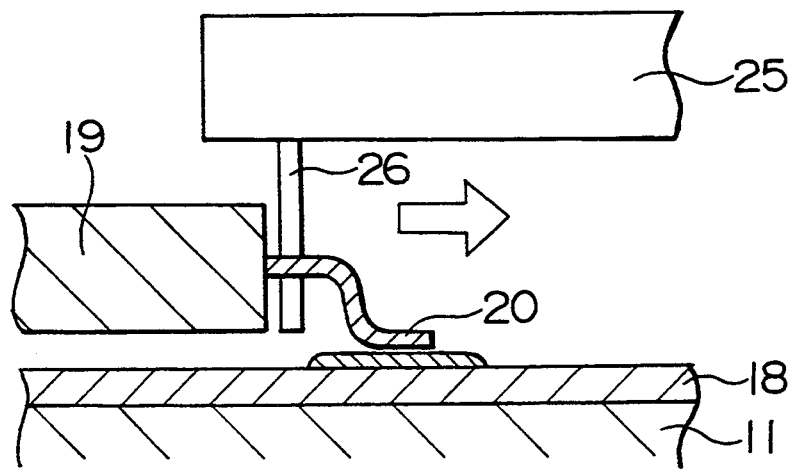
FIG. 6 is a side elevation showing one method of correcting defective outer leads.
Figure 7:
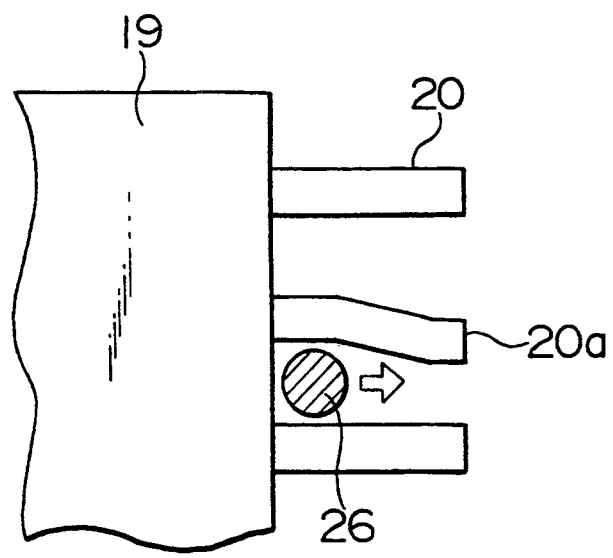
FIGS. 7 and 8 are plan views of the correcting method shown in FIG. 6.
Figure 8:
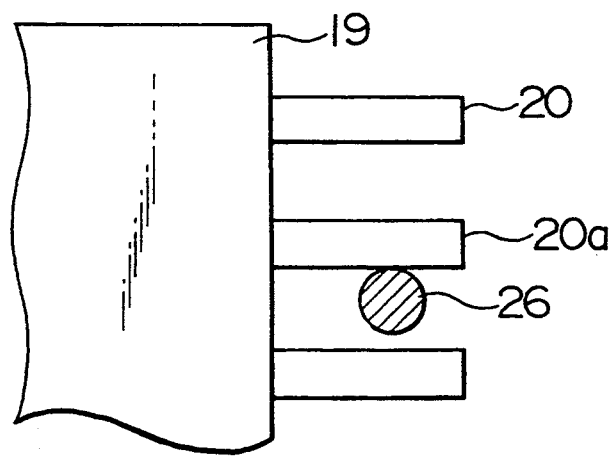

As illustrated in FIG. 5, a defective lead with a flexure and deviation can be corrected by use of a correcting device 24. The correcting device 24 has, as illustrated in FIG. 6, a correcting jig 25 fitted with a pin 26. The pin 26 is slightly thinner than the spacing between adjacent outer leads 20. This pin 26 is inserted between the adjacent outer leads 20 from roots of the outer leads 20, i.e., from the vicinity of a mold part of the IC package 19. Then, the pin 26 is so set that the tip of the pin 26 is located slightly higher than the top end of the outer lead 20. In this state, as depicted in FIG. 7, the pin 26 is shifted in the longitudinal direction of the normal outer lead 20 to the vicinity of the top end of the outer lead 20 as well as in parallel to the surface of the substrate 18. The pin 26 impinges, when shifted, on the defective lead 20a, whereby the defective lead 20a is, as depicted in FIG. 8, corrected in a normal position.

Figure 9:
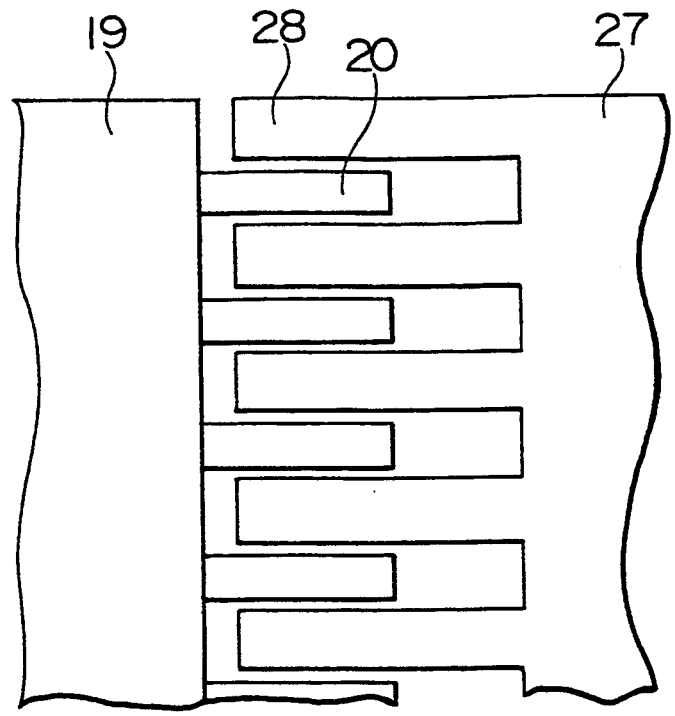
FIG. 9 is a plan view showing another method of correcting the defective outer leads.
Figure 10:
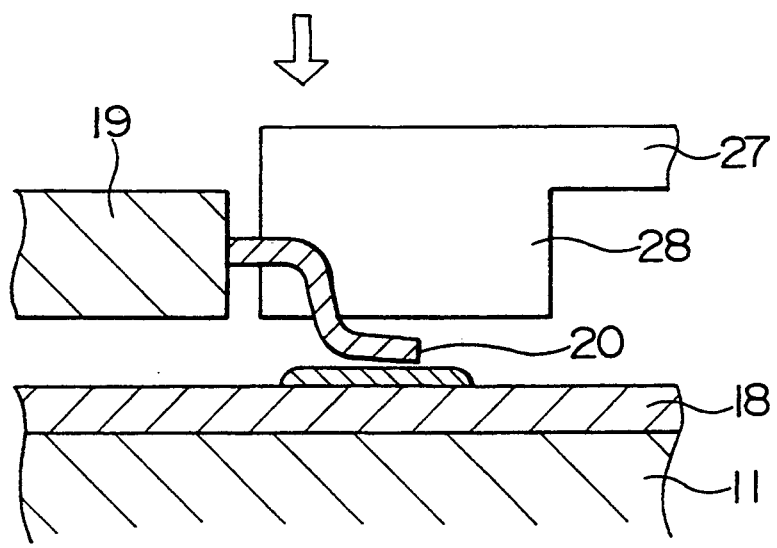
FIG. 10 is a sectional view of the correcting method shown in FIG. 9.

Further, as illustrated in FIGS. 9 and 10, a comb-like correcting jig 27 formed with a plurality of tabular correcting parts 28 is usable. The correcting jig 27 is lowered from above toward the IC package 19 so that the plurality of correcting parts 28 are interposed between the respective outer leads 20. With this descent of the correcting jig 27, the defective lead is corrected to the normal position. The correcting jig 27 may include a number correcting parts 28 corresponding to the number of the outer leads 20 extending from one side of the IC package 19, whereby the outer leads are simultaneously corrected for every side of the IC package 19. Another arrangement is that the correcting jig 27 may have a number of correcting parts 28 corresponding to the total number of the outer leads 20 of the IC package 19, whereby the outer leads are all corrected at one time with respect to all the sides of the IC package 19.

Still another arrangement is that the irradiation by the bonding laser beams may be conducted in a state where the correcting jigs 25, 27 are set in the outer leads 20 of the IC package 19; or alternatively the irradiation of the bonding laser beams may be performed with the correcting jigs 25, 27 spaced apart from the package 19 after correcting the outer leads 20.

Further, in accordance with the embodiment discussed above, the normal leads are first irradiated with the laser beams. Thereafter, the defective leads are corrected. The thus corrected leads are then irradiated with the laser beams. However, the outer leads 20 may be irradiated with the laser beams while correcting the outer leads one by one according to the need.

Figure 11A:
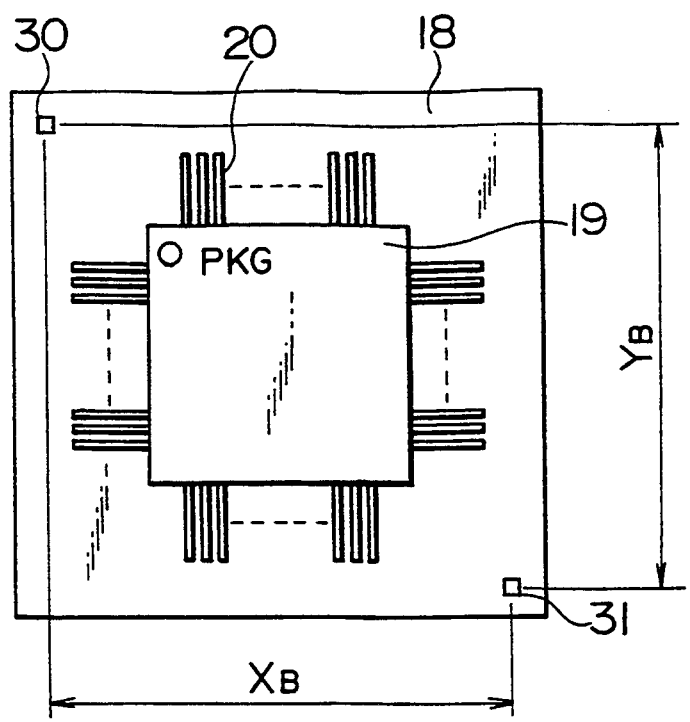
FIG. 11A is a view showing a modified example of measuring a distance between recognition marks on the substrate.

As shown in FIG. 11A, two recognition marks 30, 31 are so formed on the substrate 18 on a diagonal line in the middle of the IC package 19 between the two marks 30. When recognizing the substrate 18 through the CCD camera 13, an X-directional distance $X_B$ and a Y-directional distance $Y_B$ between these recognition marks 30, 31 are measured. A variation in pitches of the bonding lands of the substrate 18 is thereby corrected. The laser irradiation can be precisely performed. The control unit 16 calculates, if the measured distances $X_B$, $Y_B$ deviate from the preset reference value, a correction value of each bonding land position as a proportionally enlarged or contracted one of the bonding land pattern. This correction value is fed back to the program values of irradiation patterns that are stored in the memory 17. The respective outer leads 20 of the IC package 19 can be thereby exactly bonded to the bonding lands, each corresponding thereto, of the substrate 18.

Figure 11B:
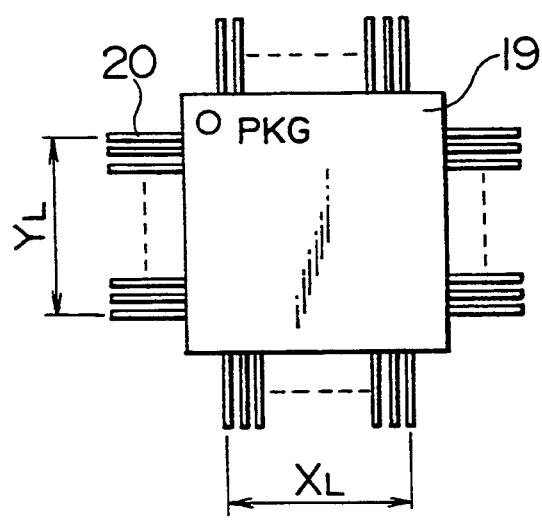
FIG. 11B is a view showing a modified example of measuring a lead-to-lead distance at both ends of an IC package.

Further, when recognizing the IC package 19 through the CCD camera 13, as shown in FIG. 11B, there are measured lead-to-lead distances $X_L$, $Y_L$ at the respective sides of the IC package 19. Variation in the pitches of the outer leads 20 can be thus corrected. The control unit 16 calculates, if the measured distances $X_L$, $Y_L$ deviate from the preset reference value, a correction value of position of each outer lead 20 of the IC package 19 as a proportionally enlarged or contracted value of the pattern of the outer lead 20 of the IC package 19. This correction value is fed back to the program values of the irradiation patterns that are stored in the memory 17.

Measured further are X- and Y-directional distances $X_B$, $Y_B$ between the recognition marks 30, 31 on the substrate 18. At the same time, the lead-to-lead distances $X_L$, $Y_L$ at both sides of the IC package 19 are measured. It is also possible to calculate a deviation quantity between the bonding land and the outer lead 20 when the IC package 19 is mounted on the substrate 18. If this deviation quantity falls within a preset allowable range, bonding by laser irradiation is performed. If beyond the allowable range, the substrate 18 or the IC package 19 is excluded as a defective product.

In some cases, the deviation quantity may exceed the allowable range due to a synergistic effect of the substrate 18 and the IC package 19. For instance, if the pitch of the bonding lands of the substrate 18 is larger than the reference value, when mounting the IC package 19 having a pitch of the outer leads 20 coincident with the reference value, the deviation quantity may fall within the allowable range. In some cases, however, the deviation quantity may exceed the allowable range, because the pitch of the outer leads 20 of the IC package 19 is smaller than the reference value. The following is a method of coping with this situation.

Allowable ranges are prescribed independently for the substrate 18 and the IC package 19. Although a total deviation quantity of a combination of the substrate 18 and the IC package 19 exceeds the allowable range, if the deviation quantity of the substrate 18 alone or IC package 19 alone is within the allowable range, each of them is temporarily excluded from the bonding object. Simultaneously, the deviation data is stored in the memory 17. The number of the substrates 18 and of the IC packages 19 for which data can be stored in the memory 17 depends on memory capacity. However, it is herein assumed that the storable number of each group of the substrates 18 and the IC packages 19 is set to 10.

If the data on the substrates 18 excluded from bonding because of the bonding pitch being too large are stored in the memory 17, and when an IC package 19 having a larger pitch of the outer leads 20 than the reference value comes out afterward, the substrate 18 having data is stored in the memory 17 combined with the IC package 19. Thus, the memory 17 always stores the data for 10 or fewer substrates 18 and of the IC packages 19 that are excluded from bonding, although the substrate 18 or the IC package 19 independently fall with the allowable range. If the number of those items excluded from the bonding object exceeds 10, the one deviating most from the reference value is excluded as a defective product.

Note that the data for the substrates 18 and the IC packages held in the memory 17 can be combined. Further, data for any one group of the substrates 18 and the IC packages 19 may be held in the memory 17. Further, this method can be executed even when the independent allowable ranges of deviations for the substrates 18 and the IC packages 19 are not prescribed.

Figure 12:
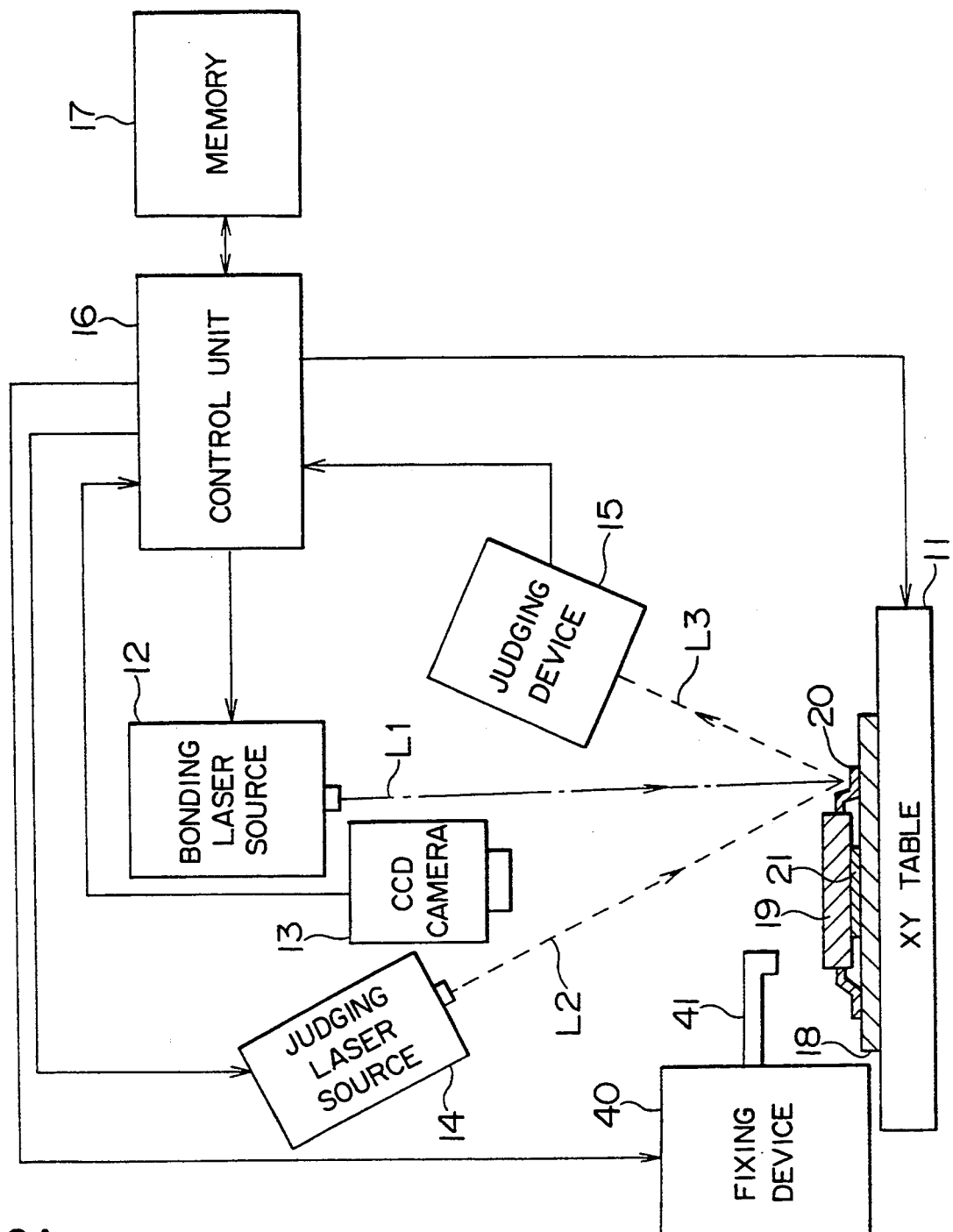
FIG. 12 is a plan view illustrating a laser OLB apparatus according to still another embodiment.
Figure 13:
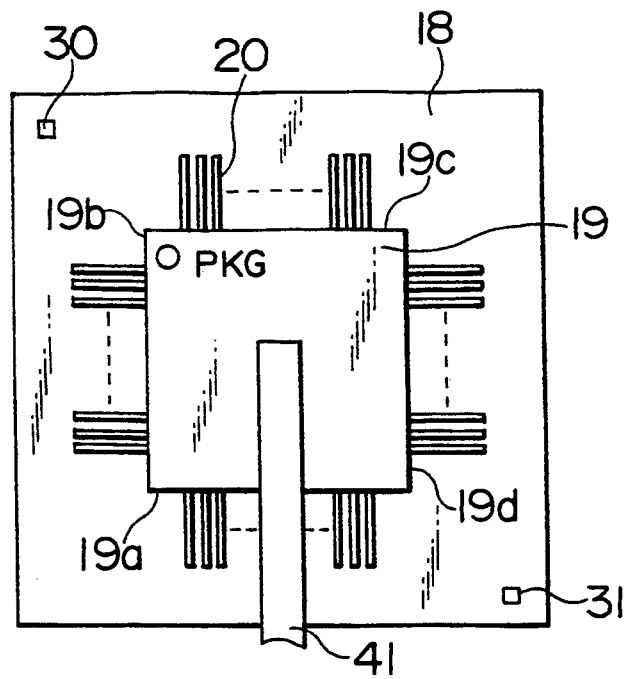
FIGS. 13 and 14 are plan views each showing a bonding method using the embodiment shown in FIG. 12.

The IC package 19 can be, as illustrated in FIG. 12, bonded using a fixing device 40 fixing the IC package 19 to the substrate 18 instead of temporarily fixing the IC package 19 to the substrate 18 with the bonding agent 21. The fixing device 40 has a movable arm 41 for pressing the IC package 19 against the substrate 18. As shown in FIG. 13, the movable arm 41 moves above the IC package from a side 19a of the IC package 19, to depress the IC package 19. At this time, some of the outer leads 20 at the side 19a are overshadowed by the arm 41. Then, in this state, to begin with, only the outer leads at the sides 19b and 19d of the IC package 19 that are positioned on the right and left sides of the arm 41 are irradiated with the laser beams and thereby bonded.

Figure 14:
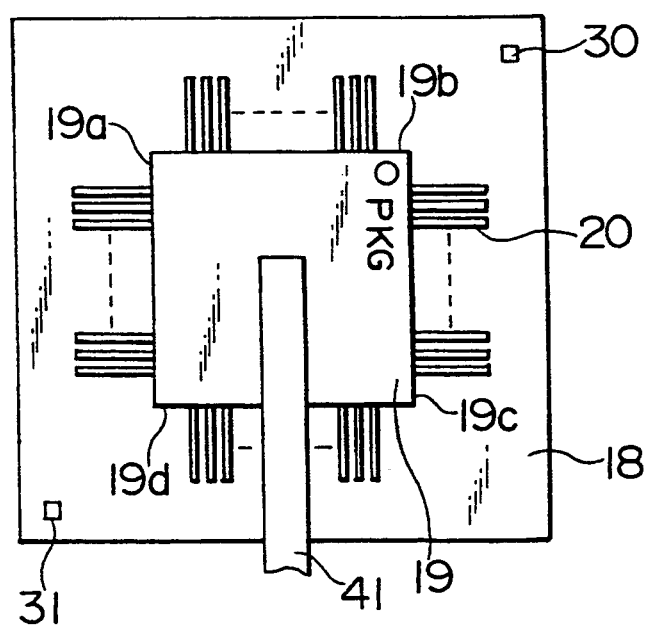

Thereafter, the arm 41 is temporarily is moved away from the IC package 19, and the XY table 11 is turned through 90°. The substrate 18 is located with an adjustment of the XY table 11 by recognizing again the recognition marks 30, 31 of the substrate 18. In this state, as illustrated in FIG. 14, the arm 41 again presses against the IC package 19. The outer leads 20 at the sides 19a, 19c of the IC package 19 that are positioned on the right and left sides of the arm 41 are irradiated with the laser beams and thereby bonded. All the outer leads 20 of the IC package 19 can be bonded in this manner. Note that the substrate 18 is again located after turning the XY table 11, and hence pattern deviation due to the turn can be prevented.

Figure 15:
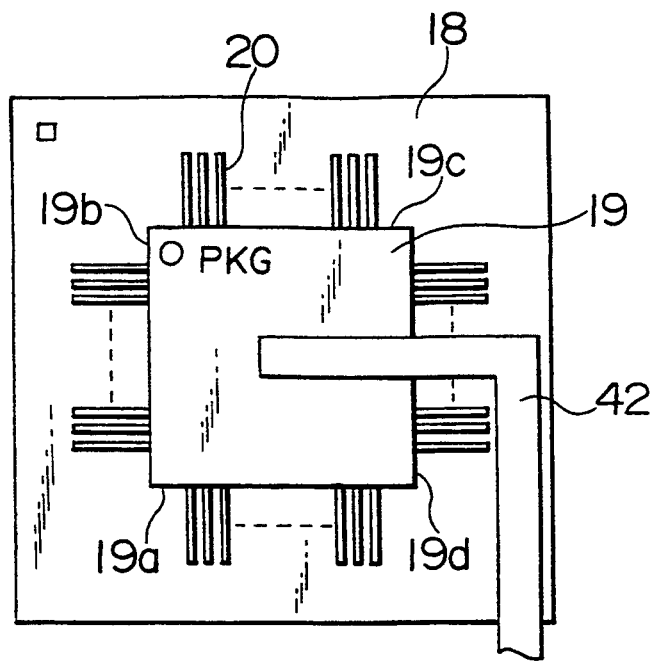
FIGS. 15–17 are plan views respectively showing other bonding methods.

Incidentally, the fixing device 40 may be fitted with a second arm 42 as shown in FIG. 15 in addition to the arm 41. In this instance, as depicted in FIG. 13, the IC package 19 is at first fixed by the first arm 41. Only the outer leads 20 at the sides 19b and 19d of the IC package 19 are bonded. Thereafter, the first arm 41 is moved away from the IC package 19. As illustrated in FIG. 15, the IC package 19 is fixed by the second arm 42. In this state, the outer leads 20 as the reminding sides 19a and 19c are bonded. This arrangement eliminates the necessity for turning the XY table 11.

Figure 16:
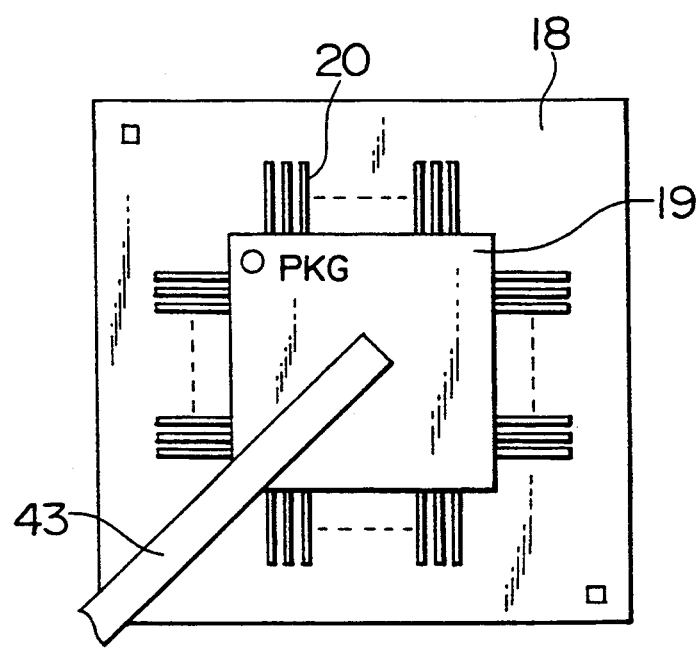

Further, as shown in FIG. 16, if there is provided a movable arm 43 positioned on a diagonal line of the IC package 19, it is possible to prevent the outer leads 20 from being overshadowed by the arm 43. All the bonding processes prevented by the arm 41 can be easily effected.

Figure 17:
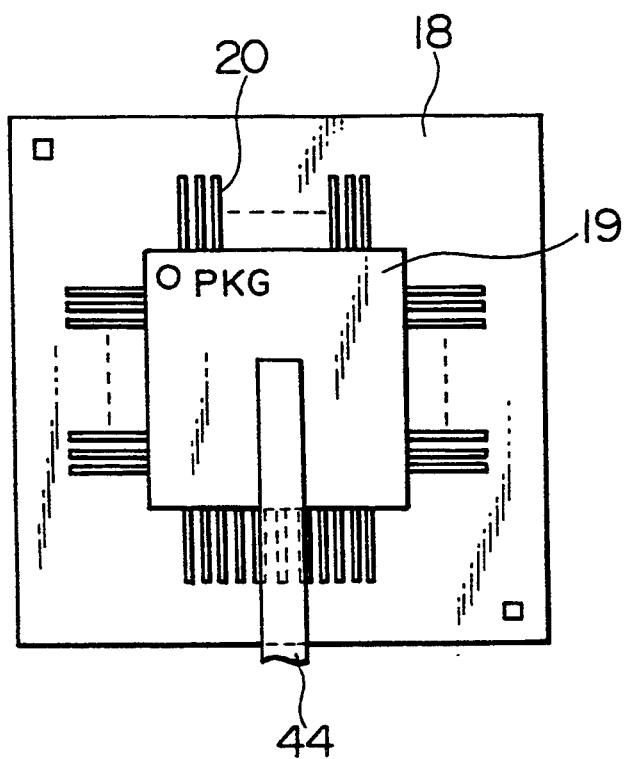

Moreover, as shown in FIG. 17, if there is employed a movable arm 44 composed of a material such as, e.g., glass that is light transmissive with respect to the bonding laser beams, the outer leads 20 positioned in the shadow of the arm 44 can be irradiated with the laser beams penetrating the arm 44. Hence, there is no necessity for turning the XY table 11 or using first and second arms.

Figure 18:
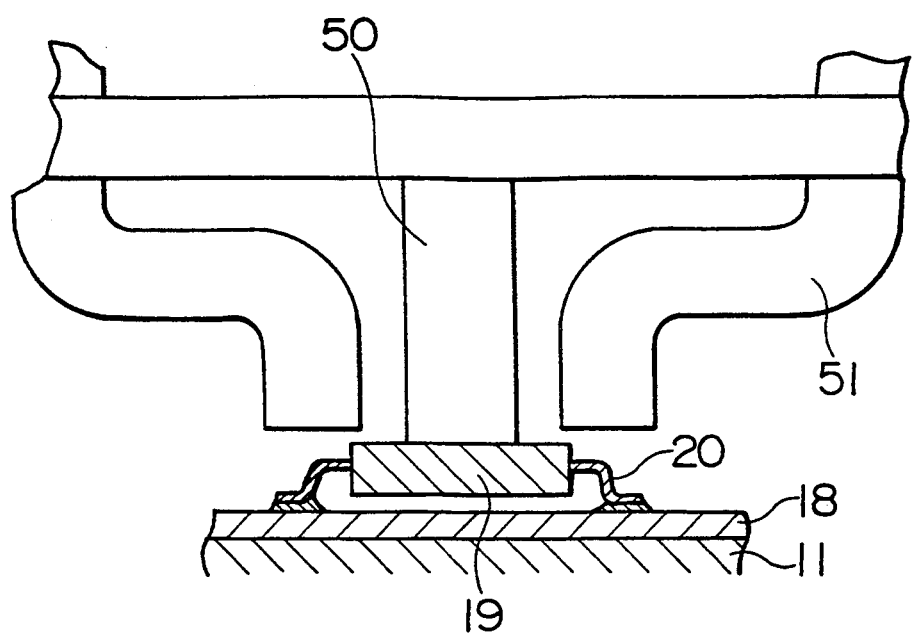
FIG. 18 is a view showing the bonding method using optical fibers.

Further, as depicted in FIG. 18, the IC package 19 may be pressed against and fixed to the substrate 18 by use of a vacuum nozzle 50 for holding and carrying the IC package 19. An additional construction may include optical fibers 51 that extend from the bonding laser source 12 to positions above the XY table 11. The bonding parts are irradiated with the bonding laser beams via the optical fibers 51. In this case, the tips of the optical fibers 51 are sequentially shifted above the plurality of outer leads 20 of the IC package 19, thus effecting the laser irradiation. In this way, the outer leads 20 overshadowed by the arm or the vacuum nozzle 50 can be irradiated with the laser beams via the optical fibers 51. Note that the outer leads 20 at the four sides of the IC package 19 can be simultaneously irradiated with the laser beams by employing a plurality of, e.g., four lines of optical fibers 51.

Figure 19:
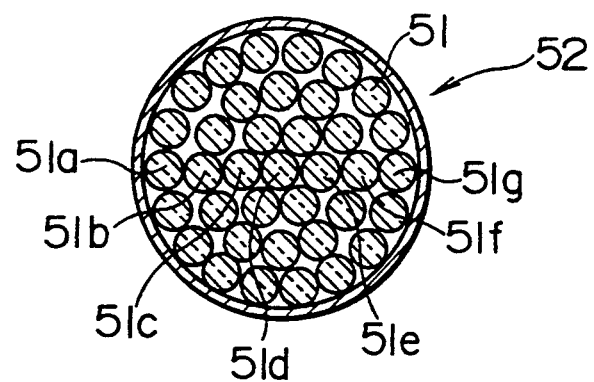
FIG. 19 is a sectional view illustrating a bundle of optical fibers.
Figure 20:
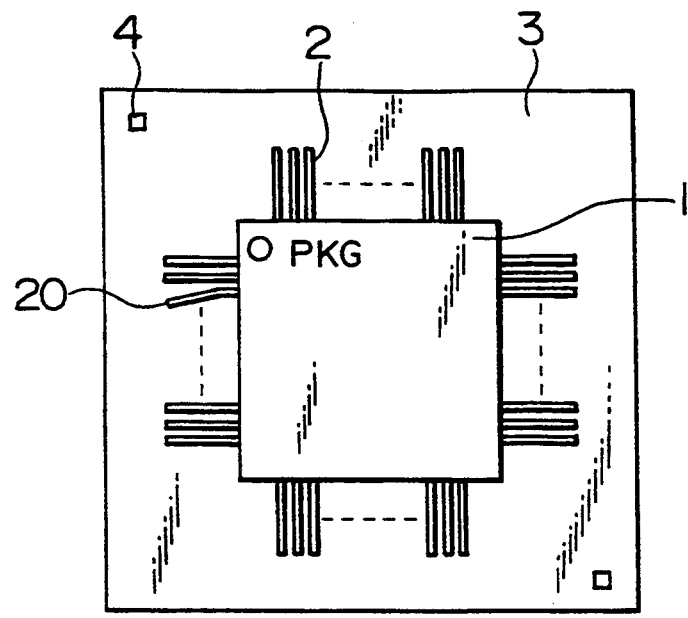
FIG. 20 is a plan view showing a conventional bonding method.
Figure 21:
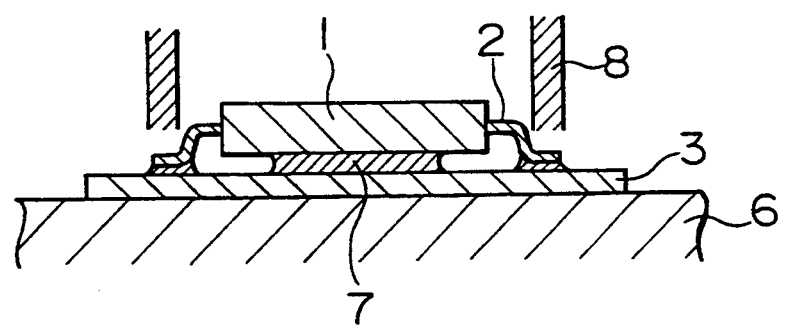
FIG. 21 is a sectional view showing the conventional bonding method.

Further, as depicted in FIG. 19, an optical fiber bundle 52 including a multiplicity of optical fibers 51 is also usable. This optical fiber bundle 52 has a sufficiently large diameter to extend over the plurality of outer leads 20 of the IC package 19. The fibers corresponding to the outer leads to be bonded are selected from the multiplicity of optical fibers 51 and transmit the laser beams. For example, optical fibers 51a–51g sequentially transmit the laser beams, whereby the plurality of outer leads 20 are sequentially bonded. Alternatively, the optical fibers 51a–51g simultaneously transmit the laser beams, whereby the plurality of outer leads 20 are also bonded.

Further, the judging laser beams emitted from the judging laser source 14 can be led to the bonding parts via the optical fibers. Still further, the direct radiation and the reflected light from the bonding part can be led to the judging device 15 via the optical fibers.

Incidentally, the bonding conditions are judged after bonding all the outer leads 20 in the embodiment shown in FIG. 1. However, the bonding condition may be judged each time a single outer lead 20 is connected. If judged to be defective, the laser beam may fall thereon each time.

It is apparent that, in this invention, a wide range of different working modes can be formed based on the invention without deviating from the spirit and scope of the invention. This invention is not restricted to specific working modes except by the appended claims.

What is claimed is:

1. A laser OLB apparatus comprising: an XY table; a bonding laser source for irradiating, with bonding laser beams, bonding parts between bonding lands of a substrate and leads of a semiconductor device that are located on the substrate, thus bonding said bonding parts;
   a light source for illuminating the bonding part between each of the leads and the bonding lands with illumination light for determining bonding conditions;
   a device for determining the bonding conditions of the bonding parts from the light reflected from the bonding parts; and
   a control unit for controlling said XY table and said bonding laser source in response to a determination made by said device.

2. The laser OLB apparatus of claim 1 wherein said device determines the bonding conditions on the basis of light intensities, in a predetermined wavelength range, of the light reflected from the bonding parts.

3. The laser OLB apparatus of claim 1 wherein said control unit controls said XY table and said bonding laser source so that bonding parts determined to be improperly bonded are irradiated again with the bonding laser beams.

4. A laser OLB apparatus comprising;
   an XY table;
   a bonding laser source for irradiating, with bonding laser beams, bonding parts between bonding lands of a substrate and leads of a semiconductor device located on the substrate, thus bonding said bonding parts;
   a recognition device for recognizing whether the leads of a semiconductor device located on the substrate are free of flexure and deviation; and
   a control unit for controlling said XY table and said bonding laser source so that only said leads recognized by said recognition device as free of flexure and deviation are bonded to corresponding bonding lands of the substrate.

5. The laser OLB apparatus of claim 4, wherein said recognition device includes a CCD camera.

6. The laser OLB apparatus of claim 4 comprising a correcting device for correcting leads of a semiconductor device on a substrate and having flexures and deviations, said control device controlling said XY table, said bonding laser source, and said correcting device so that leads recognized by said recognition device as free of flexure and deviation are irradiated directly with the bonding laser beams and said leads recognized as having flexures and deviations are irradiated with the bonding laser beams after being corrected by said correcting device.

7. The laser OLB apparatus of claim 6 wherein said correcting device includes correcting pins to be interposed between adjacent outer leads of a semiconductor device and movable in the longitudinal direction of the outer leads.

8. The laser OLB apparatus of claim 6 wherein said correcting device includes a comb-like correcting jig having tip parts to be interposed between adjacent outer leads of a semiconductor device.

9. A laser OLB apparatus comprising:
   an XY table;
   a bonding laser source for irradiating, with bonding laser beams, bonding parts between bonding lands of a substrate and leads of a semiconductor device located on the substrate, thus bonding said bonding parts;
   a recognition device for recognizing leads of a semiconductor device located on a substrate and measuring a lead-to-lead distance at each side of the semiconductor device; and
   a control unit for controlling said XY table and said bonding laser source so that said bonding parts between the leads and the bonding lands are precisely irradiated with the bonding laser beams in response to the lead-to-lead distance measured by said recognition device.

10. The laser OLB apparatus of claim 9 wherein said recognition device recognizes a plurality of recognition marks on the substrate and measures distances between the plurality of recognition marks, and said control unit calculates deviation between the leads of the semiconductor device and the bonding land of the substrate in response to the mark-to-mark distance and the lead-to-lead distance measured by said recognition device and causes said laser source to effect laser irradiation if the deviation falls within an allowable range.

11. A laser OLB apparatus comprising:
    an XY table;
    a bonding laser source for irradiating, with bonding laser beams, bonding parts between bonding lands of a substrate and leads of a semiconductor device located on the substrate, thus bonding said bonding parts;
    a fixing device including a movable arm for fixing the semiconductor device to the substrate by pressing the semiconductor device against the substrate; and
    a control unit for controlling said bonding laser source and said fixing device so that the leads at each side of the semiconductor device are irradiated with the bonding laser beams when the semiconductor device is fixed by said movable arm of said fixing device.

12. The laser OLB apparatus of claim 11 wherein said fixing device includes first and second movable arms for pressing the semiconductor device against the substrate astride the first and second sides of the semiconductor device, and said control unit controls said XY table, said bonding laser source and said fixing device so that leads at sides other than a first side of the semiconductor device are irradiated with the bonding laser beams when said first arm of said fixing device fixes the semiconductor device, and leads at sides at the first side are irradiated with the bonding laser beams when said second arm fixes said semiconductor device.

13. The laser OLB apparatus of claim 11 wherein said fixing device causes said movable arm to fix the semiconductor device on the substrate on the diagonal line of the semiconductor device.

14. The laser OLB apparatus of claim 11 wherein said movable arm of said fixing device is transmissive to the bonding laser beams emitted from said bonding laser source, and said leads overshadowed by said movable arm when said movable arm fixes the semiconductor device are irradiated by the bonding laser beams transmitted through said movable arm.

15. The laser OLB apparatus of claim 14 wherein said movable arm is glass.

16. The laser OLB apparatus of claim 11 comprising optical fibers for conducting the bonding laser beams emitted from said bonding laser source to said bonding parts between leads of the semiconductor device and the bonding lands of the substrate avoiding said movable arm of said fixing device.

17. A method of mounting a semiconductor device comprising:
    irradiating bonding parts between leads of a semiconductor device and bonding lands with bonding laser beams, thus bonding said bonding parts;
    illuminating said bonding parts between said leads and said bonding lands with illumination light for determining bonding conditions; and
    determining bonding conditions of said bonding parts from light reflected from said bonding parts between said leads and said bonding lands.

18. The method of claim 17 comprising irradiating again bonding parts determined as ill-bonded parts with the bonding laser beams.

19. A method of mounting a semiconductor device comprising the steps of:
    recognizing whether leads of a semiconductor device located on a substrate are free of flexure and deviation; and
    irradiating only said bonding parts recognized as free of flexure and deviation between said leads and said bonding lands of said substrate with the bonding laser beams, thus bonding said bonding parts.

20. The method of claim 19 comprising marking portions of said substrate which correspond to said leads recognized as having flexures and deviations.

21. The method of claim 19, further comprising the steps of correcting said leads recognized abnormal enough to cause the flexures and deviations, irradiating said bonding parts between said corrected leads and said bonding lands of said substrate with the bonding laser beams and thus bonding said bonding parts.

22. A method of mounting a semiconductor device comprising:
    sequentially recognizing whether a plurality of leads of said semiconductor device located on a substrate are free of flexure and deviation;
    irradiating with bonding laser beams bonding parts between said leads and bonding lands of said substrate recognized as free of flexure and deviation each time a lead is so recognized, thus bonding said bonding parts; and
    irradiating said bonding parts between said corrected leads and said bonding lands of said substrate with the bonding laser beams after correcting said leads recognized as having flexures and deviations, thus bonding said bonding parts.

23. A method of mounting a semiconductor device comprising:
    fixing a semiconductor device located on a substrate by pressing said semiconductor device against said substrate with an arm;

irradiating, with bonding laser beams, bonding parts between leads led at sides of said semiconductor device except sides overshadowed by said arm and bonding lands of said substrate, thus bonding said bonding parts;

releasing the pressure applied to said semiconductor device by said arm;

fixing again said semiconductor device with said arm after rotating said substrate through a predetermined angle together with said semiconductor device; and irradiating said bonding parts between said remaining leads and said bonding lands of said substrate with the bonding laser beams, thus bonding said bonding parts.

* * * * *